US006668618B2

(12) United States Patent
Larson, III et al.

(10) Patent No.: US 6,668,618 B2
(45) Date of Patent: Dec. 30, 2003

(54) SYSTEMS AND METHODS OF MONITORING THIN FILM DEPOSITION

(75) Inventors: John D. Larson, III, Palo Alto, CA (US); Herbert L. Ko, Mountain View, CA (US); Richard K. Karlquist, Cupertino, CA (US); Mark A. Hueschen, Palo Alto, CA (US); Kent W. Carey, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 111 days.

(21) Appl. No.: 09/840,401

(22) Filed: Apr. 23, 2001

(65) Prior Publication Data
US 2002/0152803 A1 Oct. 24, 2002

(51) Int. Cl.$^7$ .................. G01N 29/02; G01N 21/00; G01N 33/00; C23C 14/52
(52) U.S. Cl. ............ 73/24.01; 73/24.03; 73/24.06; 73/61.62; 427/8; 204/192.13; 204/298.03
(58) Field of Search .............. 73/24.01, 24.03, 73/24.06, 61.62; 427/10, 8, 9; 340/870.16; 204/192.13, 298.03

(56) References Cited

U.S. PATENT DOCUMENTS

| | | | |
|---|---|---|---|
| 4,362,125 A | * 12/1982 | Schadler ............... 118/712 |
| 4,543,576 A | * 9/1985 | Hieber et al. .......... 340/870.17 |
| 4,561,286 A | * 12/1985 | Sekler et al. .......... 73/24.06 |
| 4,588,942 A | 5/1986 | Kitahara |
| 4,760,351 A | * 7/1988 | Newell et al. ......... 331/48 |
| 4,962,461 A | * 10/1990 | Meyer et al. .......... 438/8 |
| 5,112,642 A | 5/1992 | Wajid |
| 5,117,192 A | 5/1992 | Hurd |
| 5,166,646 A | 11/1992 | Avanic et al. |
| 5,283,458 A | 2/1994 | Stokes et al. |
| 5,421,190 A | * 6/1995 | Brandle et al. ........ 73/30.01 |
| 5,469,742 A | 11/1995 | Lee et al. |
| 5,587,620 A | 12/1996 | Ruby et al. |
| 5,661,226 A | * 8/1997 | Bowers et al. ........ 73/24.01 |
| 5,827,952 A | 10/1998 | Mansure et al. |
| 5,852,229 A | * 12/1998 | Josse et al. ............ 73/24.06 |
| 5,859,873 A | * 1/1999 | Ritter .................. 375/259 |
| 5,873,153 A | 2/1999 | Ruby et al. |
| 5,873,154 A | 2/1999 | Ylilammi et al. |
| 5,918,258 A | * 6/1999 | Bowers ................. 73/24.06 |
| 5,932,953 A | * 8/1999 | Drees et al. ........... 310/324 |
| 5,936,150 A | * 8/1999 | Kobrin et al. ......... 73/24.06 |
| 5,942,991 A | * 8/1999 | Gaudreau et al. ...... 340/870.16 |
| 6,037,879 A | 3/2000 | Tuttle |
| 6,051,907 A | 4/2000 | Ylilammi |
| 6,060,818 A | 5/2000 | Ruby et al. |
| 6,084,503 A | * 7/2000 | Ruile et al. ............ 340/10.1 |
| 6,278,379 B1 | * 8/2001 | Allen et al. ........... 340/870.16 |
| 6,370,955 B1 | * 4/2002 | Tuller et al. ........... 73/579 |
| 6,392,562 B1 | * 5/2002 | Boston et al. ......... 340/870.28 |

FOREIGN PATENT DOCUMENTS

| | | |
|---|---|---|
| EP | 0563713 A2 * 10/1993 | |
| JP | 03279840 A * 12/1991 | ............. 73/579 |

* cited by examiner

Primary Examiner—Michael Cygan

(57) ABSTRACT

Systems and methods of monitoring thin film deposition are described. In one aspect, a thin film deposition sensor includes an acoustical resonator (e.g., a thin film bulk acoustical resonator) that has an exposed surface and is responsive to thin film material deposits on the exposed surface. A substrate clip may be configured to attach the thin film deposition sensor to a substrate. A transceiver circuit may be configured to enable the thin film deposition sensor to be interrogated wirelessly. A method of monitoring a thin film deposition on a substrate also is described.

27 Claims, 6 Drawing Sheets

SYSTEMS AND METHODS OF MONITORING THIN FILM DEPOSITION

TECHNICAL FIELD

This invention relates to systems and methods of monitoring thin film deposition.

BACKGROUND

Monitoring and controlling the deposition of thin films, for example, by vapor deposition or sputtering, are required steps in the production of high quality thin film devices. Quartz crystal deposition monitors typically are used to monitor the deposition process and to control the amount of material deposited on a substrate and the rate at which material is deposited on the substrate. In practice, a quartz crystal monitor is mounted on a water-cooled holder that is positioned inside a vacuum deposition chamber where material may deposit on the exposed monitor surface while a thin film is deposited on a substrate that is located near the exposed monitor surface. Due to the large size of the monitor crystal and the associated holder, the monitor often is mounted at a location that is offset from the substrate. As a result, the monitor typically is exposed to different deposition conditions than the substrate. This difference often is corrected by a tooling factor.

In general, as material is deposited onto the exposed surface of a quartz crystal monitor, the resonant frequency of the monitor decreases. Quartz crystal is characterized by a relatively high quality factor (Q), which enables quartz crystal monitors to make high resolution frequency measurements and, thereby, allows such monitors to detect small changes in the deposited mass. For example, a monolayer of copper added to a 6 MHz quartz crystal monitor reduces the resonance frequency by approximately 20 Hz, which is on the order of the bandwidth of the resonator. To a first order approximation, the gauge factor (MHz/nm) of a quartz crystal monitor is proportional to the density of the deposited material. Typical thin film monitor quartz crystals have quality factors that are on the order of 200,000 and, consequently, are characterized by a 3 dB line width and a frequency shift resolution that are on the order of 20 Hz. Typical commercial instruments (e.g., a quartz crystal thin film deposition monitor available from Inficon of East Syracuse, N.Y. U.S.A.) have resolutions that are on the order of 0.1–0.2 nm for film thicknesses in the range of 100 nm, or less. The absolute thickness accuracy of such systems is on the order of 1–2%.

In a typical instrumentation arrangement, the resonant frequency of a quartz crystal monitor is determined by placing the monitor in the feedback loop of an external oscillator circuit as a frequency control element. The quartz crystal monitor is connected to the oscillator circuit by a cable that extends through a vacuum feed-through in a wall of the deposition chamber. Since the equivalent electrical impedance of the quartz crystal is pure real and maximized at its parallel resonance frequency and is minimized at its series resonance frequency, the oscillator circuit tends to produce an output signal at one of the other of the crystal resonance frequencies, as determined by the external oscillator circuit. As a result, changes in the crystal resonance frequency produce corresponding changes in the oscillator circuit output frequency, which may be monitored by an external control circuit.

SUMMARY

The invention provides a novel scheme (systems and methods) for monitoring thin film thickness or substrate temperature, or both.

In one aspect, the invention features a system for monitoring a thin film deposition that includes a thin film deposition sensor comprising an acoustical resonator that has an exposed surface exposed and is responsive to thin film material deposits on the exposed surface.

Embodiments in accordance with this aspect of the invention may include one or more of the following features.

The acoustical resonator preferably is a thin film bulk acoustical resonator (FBAR). The thin film deposition sensor preferably further comprises a second acoustical resonator thermally coupled to the first acoustical resonator and shielded from deposition of thin film material. The first and second acoustical resonators may be coupled electrically in series or in parallel, or may be addressed individually. The first and second acoustical resonators may be coupled together by an electrical connection that is shielded from thin film material deposits. In one embodiment, a plurality of pairs of exposed and shielded acoustical resonators are disposed on an elongated substrate.

The monitoring system preferably includes an antenna configured to enable the thin film deposition sensor to be interrogated wirelessly. Alternatively, an optical coupler may be used to interrogate the thin film deposition sensor wirelessly.

In another aspect, the invention features a thin film deposition monitoring system that includes a thin film deposition sensor and a substrate clip that is configured to attach the thin film deposition sensor to the substrate. In this way, the monitor may be exposed to substantially the same deposition conditions as the substrate, in which case convention tooling factor corrections may not be needed.

Embodiments in accordance with this aspect of the invention may include one or more of the following features.

The substrate clip may include an antenna.

In another aspect of the invention, a thin film deposition monitoring system includes a thin film deposition sensor and a transceiver circuit that is configured to enable the thin film deposition sensor to be interrogated wirelessly.

Embodiments in accordance with this aspect of the invention may include one or more of the following features.

In some embodiments, the monitoring system may include a first antenna coupled to the thin film deposition sensor and a second antenna coupled to the transceiver circuit.

The transceiver circuit may include an energy storage element and an opto-electronic transducer.

In one embodiment, the transceiver is an RFID tag circuit.

In another aspect, the invention features a method of monitoring a thin film deposition on a substrate. In accordance with this inventive method, a thin film deposition sensor comprising an acoustical resonator is disposed within a deposition chamber, and a surface of the acoustical resonator is exposed to a thin film deposition.

Embodiments in accordance with this aspect of the invention may include one or more of the following features.

The thin film deposition sensor preferably is interrogated wirelessly to determine the resonant frequency of the acoustical resonator. The thin film deposition sensor preferably further comprises a second acoustical resonator that is shielded from the thin film deposition. The thin film deposition sensor preferably is interrogated wirelessly to determine the resonant frequencies of the first and second acoustical resonators.

In some embodiments, an optical signal may be transmitted through an optical port of the deposition chamber.

The thin film deposition sensor may be disposed within the deposition chamber by attaching the thin film deposition sensor to the substrate.

Among the advantages of the invention are the following.

The invention provides a novel thin film deposition monitoring system that may be used to monitor thin film thickness or substrate temperature, or both. The use of a pair of exposed and shielded acoustical resonators, which respond to temperature changes in substantially the same way, enables a controller to distinguish temperature-induced changes in resonant frequency from mass-induced changes in resonant frequency. This feature avoids the need to maintain the thin film deposition sensor at a constant controlled temperature and, thereby, avoids the need for a water-cooled holder and associated cooling equipment (e.g., water pipes).

In addition, the novel substrate clip provides a convenient way to implement a thin film deposition sensor as a single-use, disposable thin film thickness and temperature monitor. This feature avoids the need to periodically replace monitors and the associated risk that effluent build-up might flake off and contaminate the vacuum deposition system. Also, because the thin film deposition sensor may be clipped directly to the substrate, the invention allows a controller to monitor the film growth at the substrate surface. This feature avoids inaccuracies that could result from monitoring deposition conditions at a location displaced from the substrate, conditions which may not correlate well with the actual deposition conditions at the substrate surface. Thus, conventional tooling factor corrections may be eliminated for the most part.

Furthermore, because the novel acoustical resonators are characterized by relatively small dimensions, multiple redundant thin film deposition sensors may be disposed within a vacuum chamber to provide a plurality of data points that enable a controller to monitor and control the deposition process with greater accuracy. In this way, the deposition uniformity at the substrate surface may be monitored and controlled dynamically (e.g., in vacuum deposition systems that include multiple independently controllable material sources).

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Figure 1:
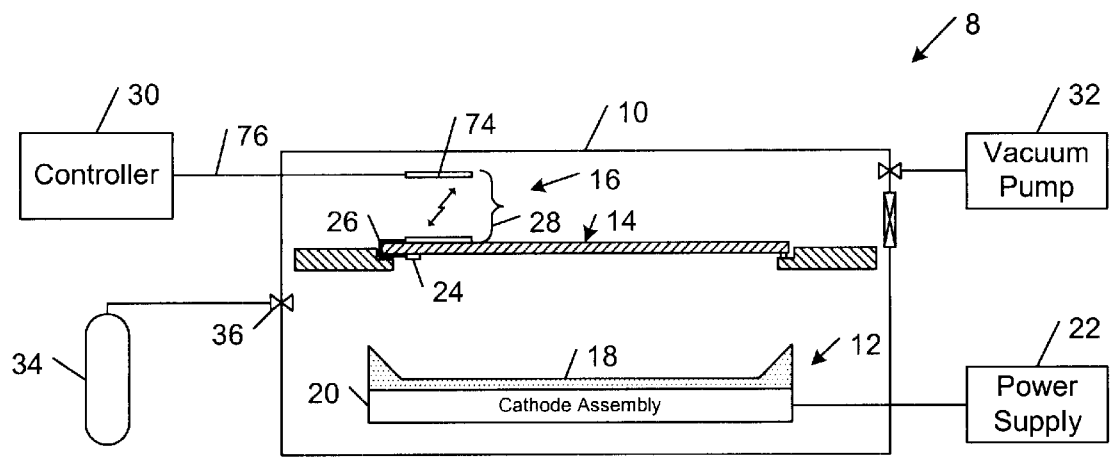
FIG. 1 is a diagrammatic side view of a vacuum deposition system that includes a target assembly for sputtering a thin film onto a substrate, and a system for monitoring the thin film deposition.

Referring to FIG. 1, in one embodiment, a vacuum deposition system 8 includes a vacuum chamber 10, a target assembly 12 for sputtering a thin film onto a substrate 14, and a system 16 for monitoring the thin film deposition. Target assembly 12 includes a target 18 that is located on a cathode assembly 20 and is formed from material (e.g., aluminum) to be deposited onto substrate 14. Cathode assembly 20 is powered by a power supply 22. Monitoring system 16 includes a thin film deposition sensor 24 that is attached to substrate 14 by a substrate clip 26, and a wireless interrogation system 28 that is configured to enable a controller 30 to wirelessly interrogate thin film deposition sensor 24.

In operation, a vacuum pump 32 evacuates vacuum chamber 10. A sputtering gas (e.g., argon) from a gas supply 34 is introduced into vacuum chamber 10 at a low pressure through a control valve 36. If reactive sputtering is to be performed, a reactive gas also is introduced into vacuum chamber 10. An electrical potential is created within vacuum chamber 10 between a system ground (anode) and target 18 and cathode assembly 20. The electrical potential may be established by grounding vacuum chamber 10 and holding the cathode at a negative potential relative to the ground potential. The resulting electric field between the cathode and the anode ionizes the support gas to form a plasma. Cathode assembly 20 generates magnetic fields that confine plasma electrons to a region between target 18 and substrate 14, thereby increasing the ion population within the plasma. The positive ions in the plasma collide with target 18, causing target material to be ejected from the surface of target 18. A portion of the ejected target material impinges onto the exposed surface of substrate 14 to form a thin film. A portion of the ejected target material also impinges onto an exposed surface of thin film deposition sensor 24, which is responsive to thin film material deposits on the exposed surface. Controller 30 may interrogate thin film deposition sensor 24 wirelessly during the thin film deposition to determine the thickness of the deposited thin film, the rate at which target material is deposited onto substrate 14, and the local substrate temperature in the vicinity of thin film deposition sensor 24. Controller 30 may use this information to control the thin film deposition process.

Figure 2:
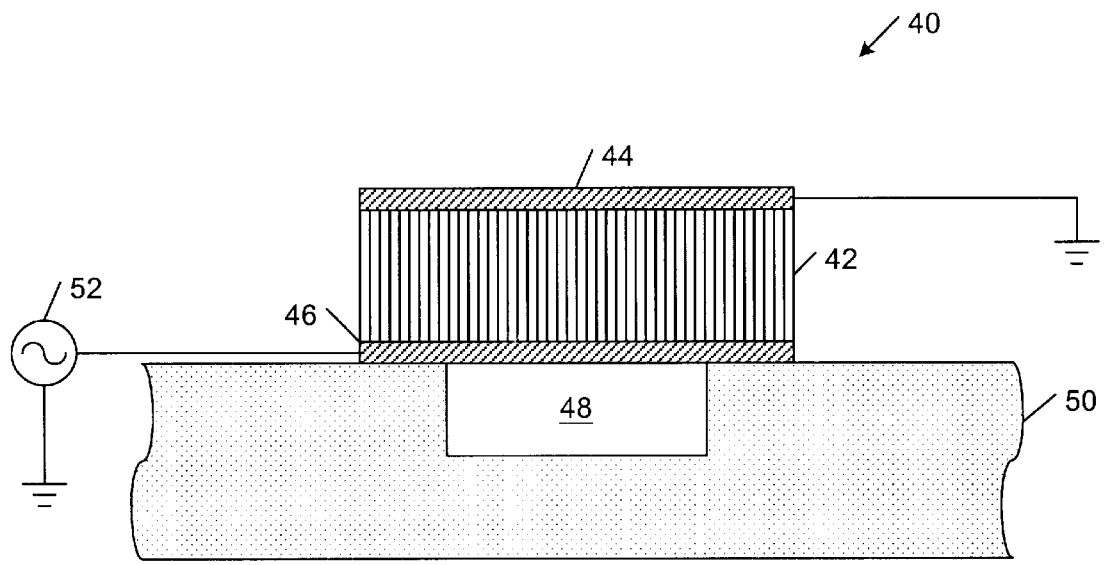
FIG. 2 is a diagrammatic cross-sectional side view of a thin film bulk acoustical resonator (FBAR).

Referring to FIG. 2, the thin film deposition sensor 24 of FIG. 1 includes one or more acoustical resonators that are configured to enable controller 30 to monitor the thin film deposition process within vacuum deposition system 8. In one embodiment, thin film deposition sensor 24 includes a thin film bulk acoustical resonator (FBAR) 40, which is formed from a thin film piezoelectric layer 42 that is sandwiched between a pair of electrodes 44, 46. Piezoelectric layer 42 may be formed from, e.g., aluminum nitride, and electrodes 44, 46 may be formed from, e.g., molybdenum. The sandwich structure is suspended over a cavity 48 that is formed in a substrate 50. FBAR 40 may be fabricated using conventional silicon micromachining techniques. In operation, a voltage supply 52 applies an electric field between electrodes 44, 46. Thin film piezoelectric layer 42 converts a portion of the applied electrical energy into mechanical energy in the form of sound waves. The sound waves propagate in the direction of the applied electric field and reflect off the interface between cavity 48 and electrode 46, return through piezoelectric layer 42 and re-reflect off the interface between the air and electrode 44. FBAR 40 is characterized by a mechanical resonant frequency corresponding to the frequency at which the half wavelength of a sound wave propagating in the device is approximately equal to the total thickness of the device for a given velocity of sound in the FBAR.

Further details regarding the construction and operation of thin film acoustical resonators may be obtained from U.S. Pat. Nos. 5,587,620, 5,873,153 and 6,060,818, each of which is incorporated herein by reference.

Figure 3:
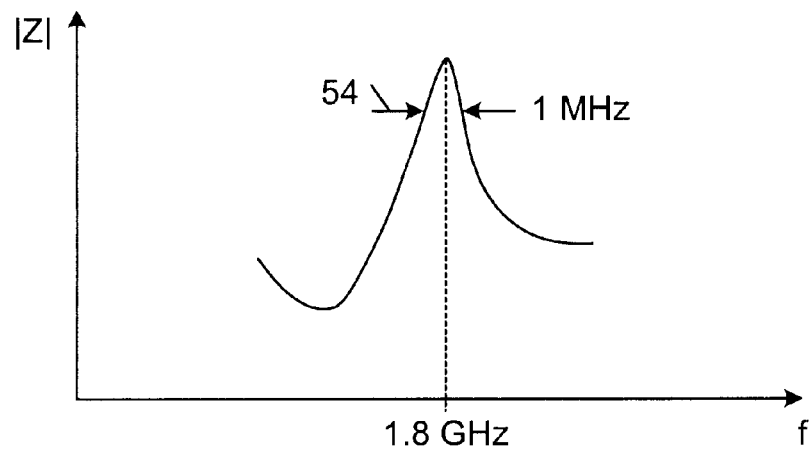
FIG. 3 is a graph of the magnitude of electrical impedance (|Z|) of the FBAR of FIG. 2 plotted as a function of frequency (f) and indicating the series and shunt resonant frequencies.

As shown in FIG. 3, at the mechanical resonance, FBAR 40 appears to be an electronic resonator with an electrical impedance (Z) that peaks at the resonant frequency (e.g., 1.8 GHz). The resonant frequency is established, at least in part, by the physical dimensions of FBAR 40. For applications in the microwave frequency range (e.g., about 1.8 GHz to about 5 GHz), FBAR 40 may have physical dimensions on the order of 150 $\mu$m×150 $\mu$m in area and 0.5 $\mu$m to 5 $\mu$m thickness. In operation, FBAR 40 is characterized by a relatively high gauge factor as a result of its relatively high resonant frequency. For example, FBARs with a resonant frequency of about 1.8 GHz typically exhibit quality factors on the order of about 2,000, which is equivalent to a line-width 54 that is on the order of about 1 MHz and a gauge factor to deposited film thicknesses that is on the order of about 1 MHz frequency shift per 0.5 $\mu$m of deposited film thickness. Such an FBAR construction may produce a detectable frequency shift corresponding to a few tenths of a nm of deposited material. For example, a deposition of 200 nm of molybdenum typically produces a 400 MHz downshift in resonant frequency (i.e., a 22% downshift from the initial resonant frequency of 1.8 GHz). Such a resonant frequency downshift may be detected by any one of a wide variety of microwave instrumentation techniques. In addition, since FBAR 40 converts the deposited film thickness increase into a change in resonant frequency, controller may convert the thickness and deposition rate information automatically into digital values that may be used in subsequent data processing steps.

Figure 4A:
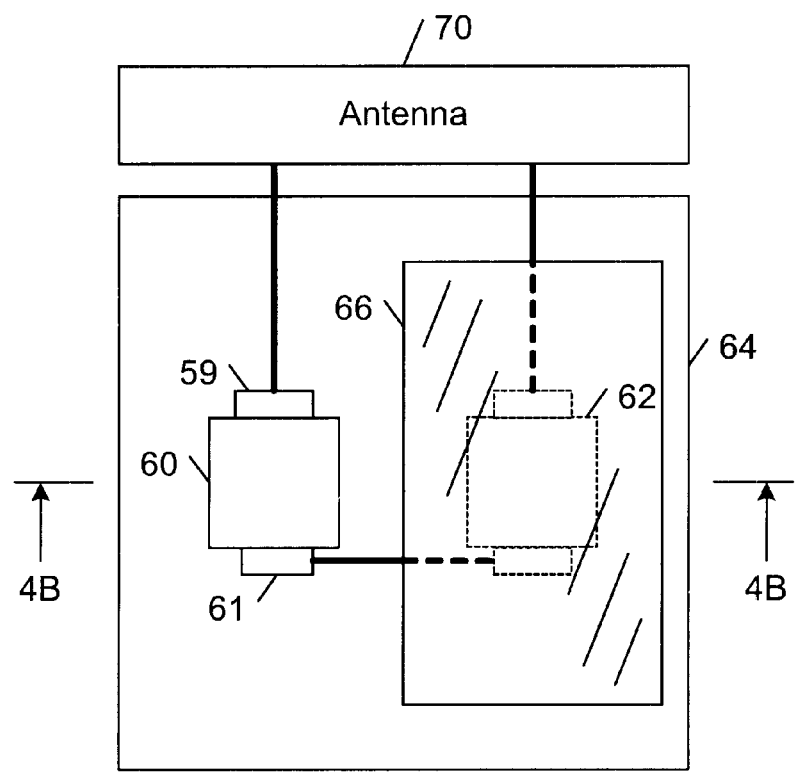
FIG. 4A is a diagrammatic top view of a thin film deposition sensor incorporating two FBARs that are connected electrically in series.
Figure 4B:
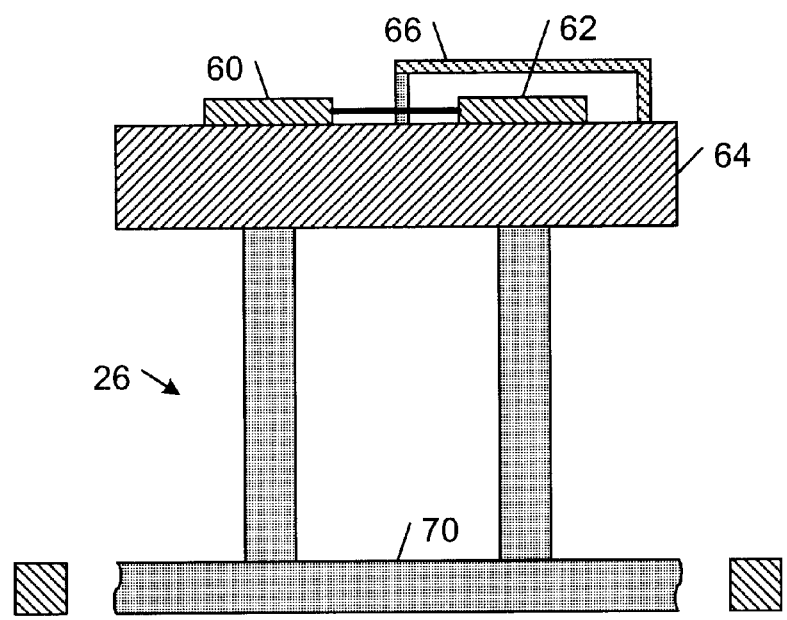
FIG. 4B is a diagrammatic cross-sectional side view of the thin film deposition sensor of FIG. 4A and a substrate clip that is configured to attach the thin film deposition sensor to a substrate.
Figure 4C:
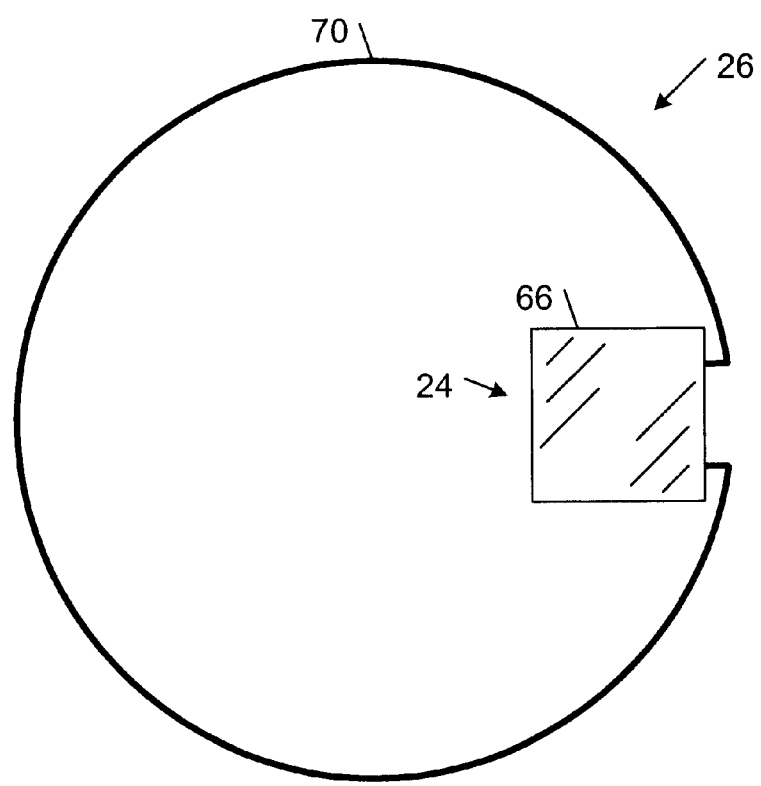
FIG. 4C is a diagrammatic bottom view of the thin film deposition sensor of FIG. 4A and the substrate clip of FIG. 4B.
Figure 5:
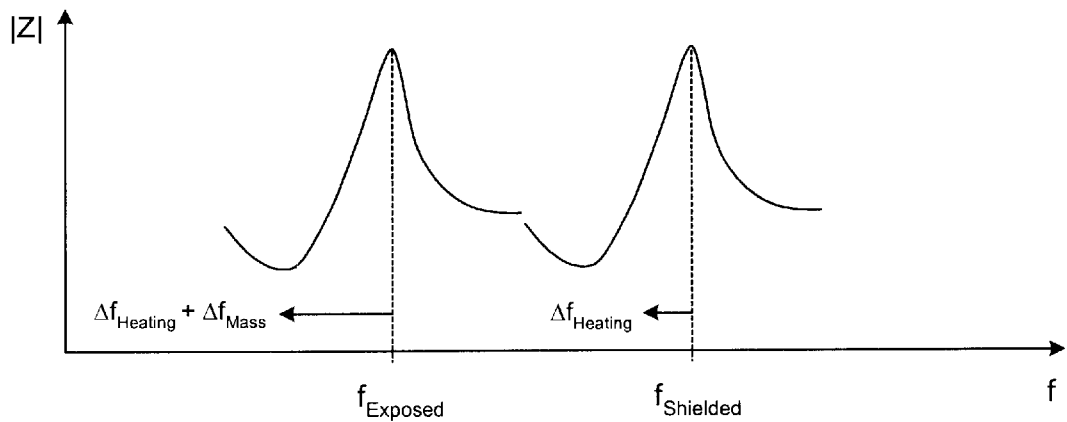
FIG. 5 is a graph of the magnitude of electrical impedance (|Z|) of the thin film deposition sensor of FIG. 4A plotted as a function of frequency (f) during a thin film deposition.

Referring to FIGS. 4A–4C and 5, in one embodiment, thin film deposition sensor 24 includes a pair of FBARs 60, 62, which are mounted on a thermally conductive substrate 64 (e.g., a silicon substrate) with an areal dimension of about 1 mm×1 mm. FBARs 60, 62 are connected electrically in series. In other embodiments, FBARs 60, 62 may be connected in parallel or addressed individually. FBARs 60, 62 are configured to enable controller 30 to distinguish temperature-induced changes in resonant frequency from mass-induced changes in resonant frequency. In particular, FBAR 60 is exposed to receive material deposits from target 18, whereas FBAR 62 is shielded from such deposits by a deposition shield 66. Referring to FIG. 5, during a thin film deposition, exposed FBAR 60 would be subject to the frequency downshifting effects of mass loading ($\Delta f_{Exposed, Mass}$) and heating ($\Delta f_{Exposed, Heating}$) which is approximately 5 MHz downshift per 100° C. increase in temperature. Shielded FBAR 60, on the other hand, would be subject to only the frequency downshifting effects of heating ($\Delta f_{Shielded, Heating}$). Because the exposed and shielded FBARs 60, 62 are matched and thermally coupled together, the heat-induced frequency downshifts observed in exposed FBAR 60 track the frequency downshifts observed in shielded FBAR 62. Controller 30 may compute the amount of material deposited on substrate 14 and the rate at which material is deposited on substrate 14 based upon the difference between the resonant frequencies of the exposed and shielded FBARs 60, 62:

$$\Delta f_{Exposed} - \Delta f_{Shielded} = \Delta f_{Exposed, Mass} + \Delta f_{Exposed, Heating} - \Delta f_{Shielded, Heating} = \Delta f_{Exposed, Mass}$$

In addition, controller 30 may track the resonant frequency of shielded FBAR 62 to determine the local temperature of substrate 14. Thin film deposition sensor 24 may be characterized by a temperature resolution of approximately 1–2° C. and a linearity up to at least 100° C. At temperatures above 100° C., the temperature of thin film deposition sensor 24 may be determined from an empirically derived lookup table. In this way, thin film deposition sensor 24 may act as a thin film thickness monitor and a temperature monitor.

As mentioned above, thin film deposition sensor 24 also includes a substrate clip 26 that is formed from a resilient material and is configured to attach thin film deposition sensor 24 securely to substrate 14. In one embodiment, substrate clip 26 is designed to clip onto the peripheral edge of substrate 14. In operation, substrate clip 26 may be clipped to substrate 14 before substrate 14 is loaded into vacuum deposition chamber 10 and may be detached from substrate 14 and discarded after substrate 14 is unloaded from vacuum deposition chamber 10. In this way, substrate clip 26 provides a convenient way to implement thin film deposition sensor 24 as a single-use, disposable thin film thickness and temperature monitor.

As shown in FIGS. 4A–4C, substrate clip 26 also may incorporate an antenna 70 that is configured to enable controller 30 to interrogate thin film deposition sensor 24 wirelessly. Antenna 70 may be implemented as a loop antenna (e.g., a ¼ wavelength circumference loop antenna), as shown. Alternatively, antenna 70 may be implemented as a dipole antenna (e.g., a ½ wavelength dipole antenna) that preferably projects out of the plane of the backside of substrate 14 (although, in some embodiments, the dipole antenna may be oriented in a plane parallel to the backside of substrate 14). For communications in the microwave range (e.g., at 1.88 GHz, 2.45 GHz, or the unlicensed bands around 5 GHz), antenna 70 may have dimensions on the order of a few centimeters. In operation, controller 30 may establish a microwave radio link with thin film deposition sensor 24 through an interrogation antenna 74, which is coupled to controller 30 by a coaxial cable 76 that extends through a vacuum feed-though in vacuum chamber 10 (see FIG. 1). In one embodiment, controller 30 includes an interrogation transmitter and an interrogation receiver. The interrogation transmitter is configured to interrogate thin film deposition sensor 24 by transmitting a microwave signal of a few watts of input power that is a gated sine burst of the resonant frequency of exposed FBAR 60 or shielded FBAR 62. The duration of the burst preferably is long enough to excite the resonator to be interrogated, but short enough to allow time to monitor the natural resonance of the resonator. For example, a burst of about 100–1,000 cycles of the resonant frequency of a desired resonator 60, 62 to be interrogated may be transmitted from interrogation antenna 74. After the burst has been transmitted, the interrogation transmitter is turned off and signals from the interrogation receiver are monitored by controller 30 to detect the current natural ringing frequency (series or shunt resonance) of the excited resonator as it exponentially decays. Since the period of a 1.8 GHz sine wave is 556 picoseconds, a ten-cycle burst may be completed in 55.6 nanoseconds. On the other hand, the 1/e decay time of an FBAR with a quality factor of 2,000 is on the order of 1,000 nanoseconds. Thus, in this embodiment, the resonant frequency of an interrogated FBAR may be determined within a few microseconds. Consequently, the resonant frequencies of both FBARs 60, 62 may be determined with a data rate of approximately 50–100 kHz, with ample time between measurements to process data received from thin film deposition sensor 24.

Other embodiments are within the scope of the claims.

The embodiment of FIGS. 4A–4C and 5, may be used to monitor the deposition of electrically insulating films. For the deposition of electrically conducting films, a thin dielectric layer may be disposed over sensor 24 to prevent shorting of the exposed electrode bonding pads 59, 61.

Figure 6A:
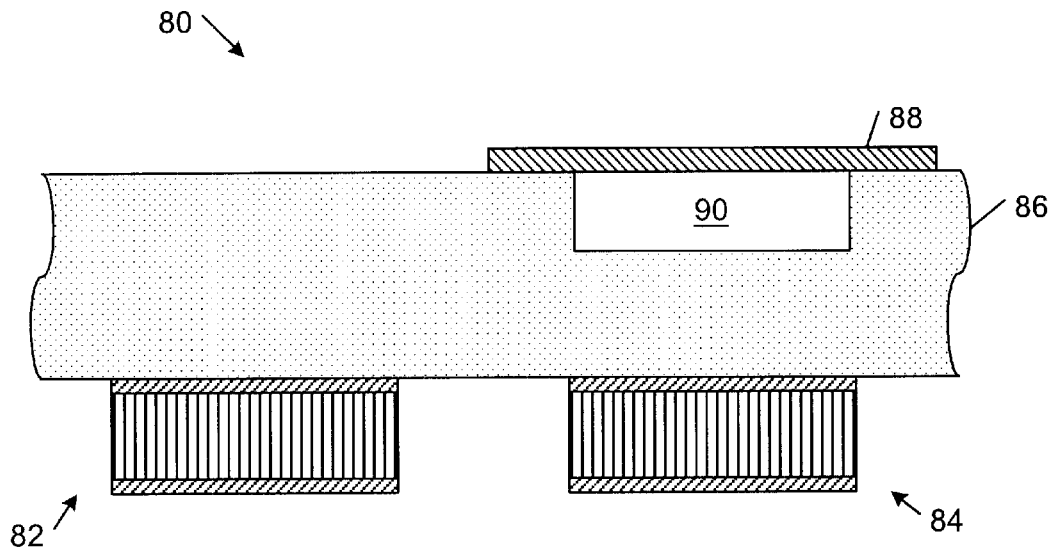
FIG. 6A is a diagrammatic cross-sectional side view of another thin film deposition sensor.

Referring to FIG. 6A, in another embodiment, a thin film deposition sensor 80 includes a pair of FBARs 82, 84, which are mounted on a thermally conductive substrate 86 (e.g., a silicon substrate) with an areal dimension of about 1 mm×1 mm. FBARs 82, 84 are connected electrically in series. In other embodiments, FBARs 82, 84 may be connected in parallel or addressed individually. FBARs 82, 84 are configured to enable controller 30 to distinguish temperature-induced changes in resonant frequency from mass-induced changes in resonant frequency and may be used for depositions of electrically insulating and electrically conducting films without modification. In particular, FBARs 82 and 84 are mounted on the backside of substrate 86 such that their bonding pads and electrical connections are shielded from sputtered material deposits. However, the region of the top surface of substrate 86 corresponding to the front side of FBAR 82 is exposed to receive material deposits from target 18, whereas the region of the top surface of substrate 86 corresponding to the front side of FBAR 84 is shielded from such deposits by a deposition shield 88 (e.g., an AlN thin film layer) that is formed over an isolation cavity 90. Thus, during a thin film deposition, exposed FBAR 82 would be subject to the frequency downshifting effects of mass loading ($\Delta f_{Exposed, Mass}$) and heating ($\Delta f_{Exposed, Heating}$). Shielded FBAR 84, on the other hand, would be subject to only the frequency downshifting effects of heating ($\Delta f_{Shielded, Heating}$). Because the exposed and shielded FBARs 82, 84 are matched and thermally coupled together, the heat-induced frequency downshifts observed in exposed FBAR 82 track the frequency downshifts observed in shielded FBAR 84. Controller 30 may compute the amount of material deposited on substrate 14 and the rate at which material is deposited on substrate 14 based upon the difference between the resonant frequencies of the exposed and shielded FBARs 82, 84, as explained above. In addition, controller 30 may track the resonant frequency of shielded FBAR 84 to determine the local temperature of substrate 14. In this way, thin film deposition sensor 80 may act as a thin film thickness monitor and a temperature monitor.

Figure 6B:
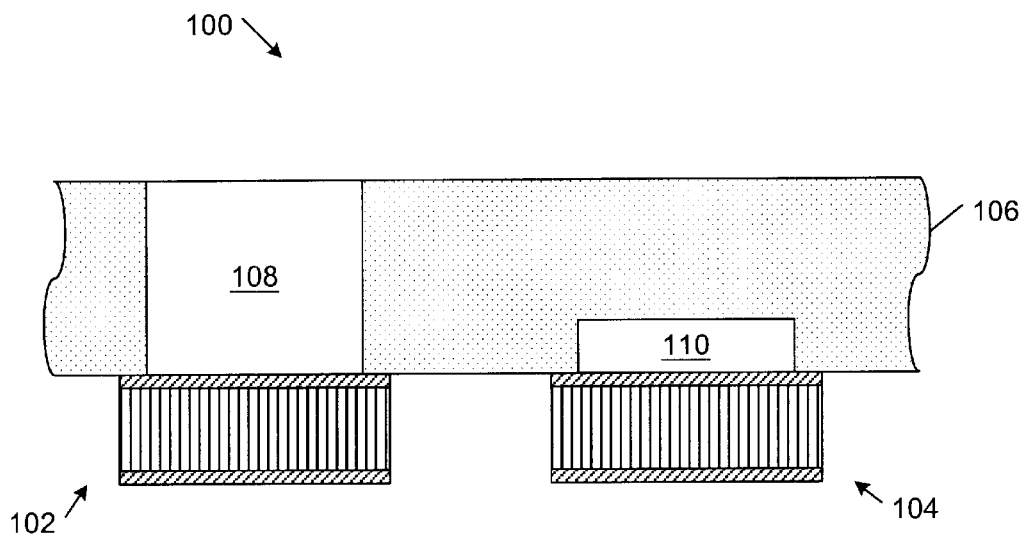
FIG. 6B is a diagrammatic cross-sectional side view of another thin film deposition sensor.

As shown in FIG. 6B, in another embodiment, a thin film deposition sensor 100 includes a pair of FBARs 102, 104, which are mounted on a thermally conductive substrate 106 (e.g., a silicon substrate) with an areal dimension of about 1 mm×1 mm. FBARs 102, 104 are connected electrically in series. In other embodiments, FBARs 102, 104 may be connected in parallel or addressed individually. FBARs 102, 104 are configured to enable controller 30 to distinguish temperature-induced changes in resonant frequency from mass-induced changes in resonant frequency and may be used for depositions of electrically insulating and electrically conducting films without modification. In particular, FBARs 102 and 104 are mounted on the backside of substrate 106 such that their bonding pads and electrical connections are shielded from sputtered material deposits. However, the front side of FBAR 102 is exposed to receive material deposits from target 18 through a through-hole 108 in substrate 106, whereas the front side of FBAR 104 is shielded from such deposits by the portion of substrate 106 above an isolation cavity 110. Thus, during a thin film deposition, exposed FBAR 102 would be subject to the frequency downshifting effects of mass loading ($\Delta f_{Exposed, Mass}$) and heating ($\Delta f_{Exposed, Heating}$). Shielded FBAR 104, on the other hand, would be subject to only the frequency downshifting effects of heating ($\Delta f_{Shielded, Heating}$). Because the exposed and shielded FBARs 102, 104 are matched and thermally coupled together, the heat-induced frequency downshifts observed in exposed FBAR 102 track the frequency downshifts observed in shielded FBAR 104. Controller 30 may compute the amount of material deposited on substrate 106 and the rate at which material is deposited on substrate 106 based upon the difference between the resonant frequencies of the exposed and shielded FBARs 102, 104, as explained above. In addition, controller 30 may track the resonant frequency of shielded FBAR 104 to determine the local temperature of substrate 106. In this way, thin film deposition sensor 100 may act as a thin film thickness monitor and a temperature monitor.

Figure 7:
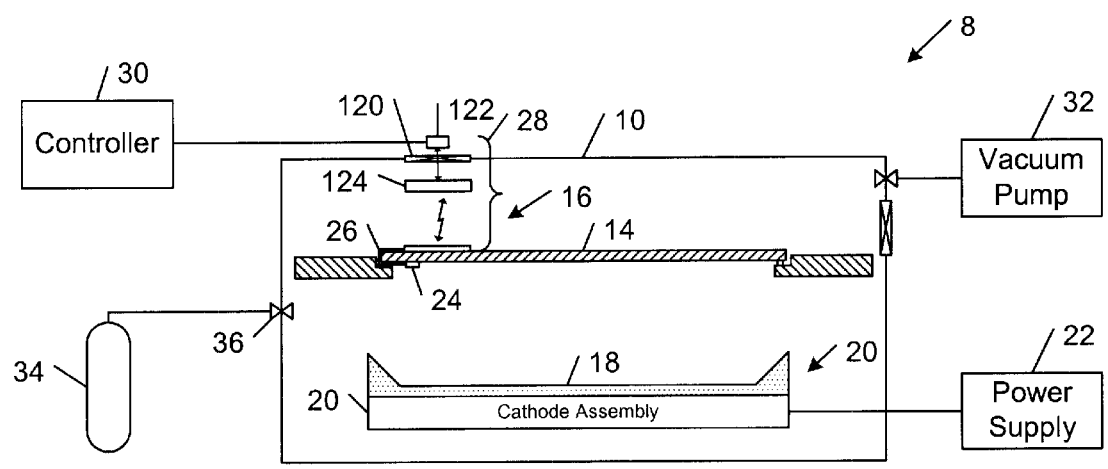
FIG. 7 is a diagrammatic side view of a vacuum deposition system that includes an optical system for interrogating the thin film deposition sensor of FIG. 4A.
Figure 8:
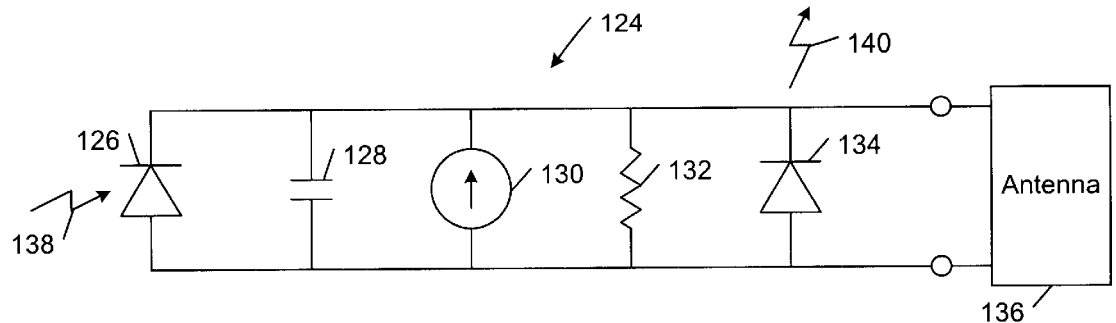
FIG. 8 is a circuit diagram of an interrogation transceiver circuit that is configured to enable the optical system of FIG. 7 to interrogate the thin film deposition sensor of FIG. 4A wirelessly.

Referring to FIGS. 7 and 8, in one embodiment, wireless interrogation system 28 may be configured to communicate optically through an optical port 120 in vacuum chamber 10 and, thereby, avoid the vacuum feed-through that is required for a direct coaxial cable connection. In this embodiment, controller 30 communicates with an optical transceiver 122 that is configured to exchange light signals with an interrogation transceiver circuit 124 through optical port 120.

As shown in FIG. 8, optical transceiver circuit 124 includes an optical receiver 126 (e.g., an opto-electronic transducer, such as a p-i-n photodiode), a capacitor 128, a current driver 130, a resistor 132, and an optical transmitter 134 (e.g., an opto-electronic transducer, such as a p-i-n photodiode). Current driver 130 is configured to drive an electrical current through an interrogation antenna 136 at a frequency that may be swept through a predetermined frequency range encompassing the resonant frequencies of FBARs 60, 62. In operation, controller 30 directs optical transceiver 122 to transmit an optical signal 138 to interrogation transceiver circuit 124. Optical receiver 136 converts the transmitted optical signal 138 into DC electrical energy, which is stored in capacitor 128. The transmitted optical signal 138 preferably charges capacitor 128 with sufficient energy to enable current driver 130 to sweep the current applied to antenna 136 through the predetermined frequency range one or more times. Interrogation antenna 136 converts the applied current into a microwave gated sine burst signal that may be used to interrogate thin film deposition sensor 24, as described above. Resistor 132 converts the exponential decay signals received from the excited thin film deposition sensor 24 into corresponding voltage signals. Optical transmitter 134 transmits to optical transceiver 122 optical signals 140 corresponding to the voltage signals established across resistor 132. Controller 30 may extract from optical signals 140 the resonant frequencies of FBARs 60, 62, from which controller 30 may determine the amount of material deposited on substrate 14, the rate at which material is deposited on substrate 14 and the temperature of substrate 14, as described above.

In one embodiment, interrogation transceiver circuit 124 may be mounted on substrate clip 26 and electrically coupled to thin film deposition sensor 24. In this embodiment, thin film deposition sensor antenna 70 and interrogation antenna 136 are not required. Optical transceiver 122 preferably supplies sufficient power to interrogation transceiver circuit 124 to excite FBARs 60, 62 directly.

In another embodiment, vacuum chamber 10 may include an interrogation arm that is configured to couple electrically to thin film deposition sensor 24 after substrate 14 has been loaded into the chamber. The interrogation arm may couple electrically to thin film deposition sensor 24 through substrate clip 26 or may directly contact electrical leads mounted on sensor substrate 64. The interrogation arm may be coupled to a coaxial cable that extends through a vacuum feed-though in vacuum deposition chamber 10. In this embodiment, controller 30 may interrogate thin film deposition sensor 30 directly through the interrogation arm.

Figure 9:
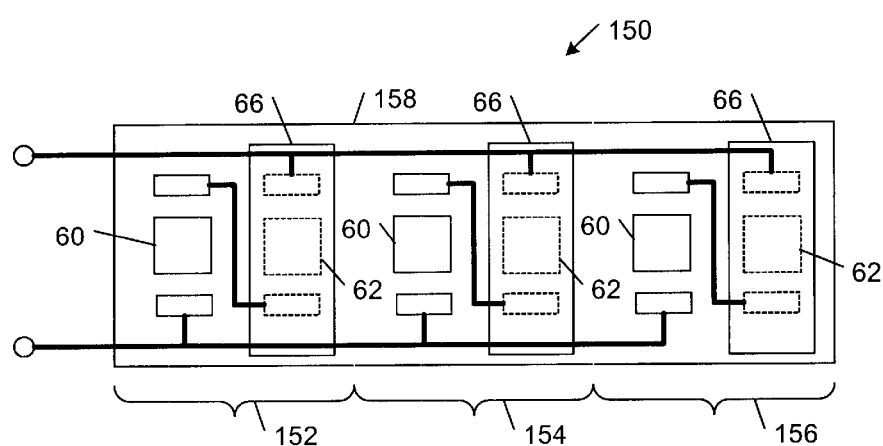
FIG. 9 is a diagrammatic top view of an elongated thin film deposition sensor that includes multiple FBAR series pairs that are connected electrically in parallel.

As mentioned above, thin film deposition sensor 24 may include one or more acoustical resonators. In some embodiments, a thin film deposition sensor may include multiple, redundant pairs of exposed and shielded acoustical resonators. The redundant pairs of acoustical resonators may be arranged on the surface of a substrate in a wide variety of different ways. Referring to FIG. 9, in one embodiment, a thin film deposition sensor 150 may include an array of sensor series pairs 152, 154, 156 that are connected electrically in parallel and disposed on an elongated substrate 158. Thin film deposition sensor 150 may be attached to substrate 14 by substrate clip 26 and oriented radially along the exposed surface of substrate 14. In this way, thin film deposition sensor 150 enables controller 30 to monitor variations in deposition thickness, deposition rate and temperature across the surface of substrate 14. Thin film deposition sensor 150 may be used in combination with an elongated deposition shield with a window that is configured to selectively expose a single acoustical resonator to the sputtering conditions inside vacuum deposition chamber 10.

Although the interrogation antennas 74, 136 are located within vacuum chamber 10 in the above-described embodiments, the interrogation antennas may be positioned outside vacuum deposition chamber 10 in other embodiments provided there is sufficient coupling between the interrogation antennas and antenna 70 of thin film deposition sensor 24. Furthermore, more than one thin film deposition sensor 24 may be attached to substrate 14.

The above-described thin film deposition sensors may be interrogated wirelessly in a ways that differ from the interrogation schemes described above.

Figure 10:
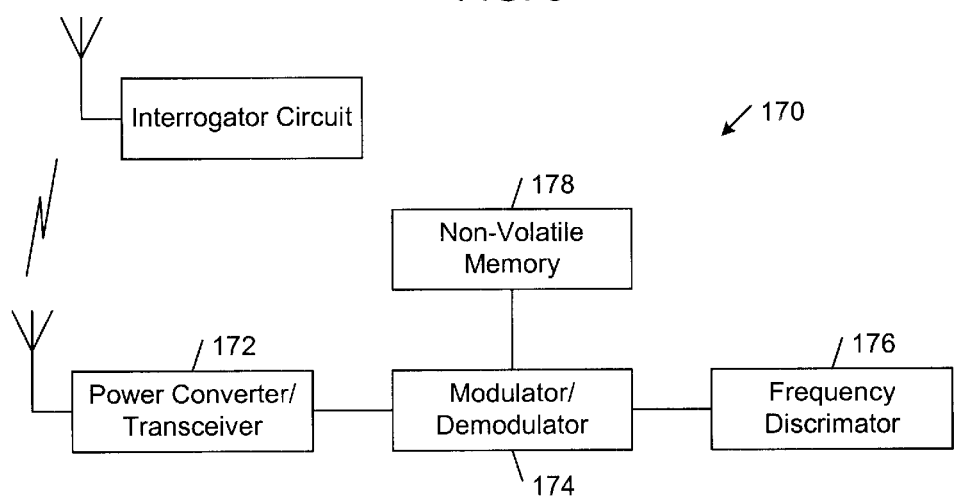
FIG. 10 is a block diagram of an RFID tag circuit.

Referring to FIG. 10, in one wireless interrogation scheme, a thin film deposition sensor may be incorporated into an RFID tag circuit 170 that includes a power converter/transceiver 172, a modulator/demodulator circuit 174, a frequency discriminator 176, and a non-volatile memory 178. Power converter/transceiver 172 rectifies an RF signal received from an interrogator circuit to provide DC power to the components of RFID tag circuit 170. In operation, non-volatile memory 178 may send to modulator/demodulator 174 data (e.g., a serial number) identifying the associated thin film deposition sensor. This data is transmitted to the interrogator circuit, which is configured to recover the data. Data corresponding to response signals from frequency discriminator 176 also is transmitted to the interrogator circuit. In particular, frequency discriminator 176 preferably is implemented as a Foster-Seeley discriminator that includes a pair of diodes and a sensor FBAR operating as bandpass filter. Frequency discriminator 176 preferably is configured such that the DC output is proportional to the frequency difference between the interrogation frequency and the sensor FBAR resonant frequency and is zero when interrogated at the sensor FBAR resonant frequency. Other embodiments may include different discriminator implementations. The interrogator circuit preferably includes a servo loop that is configured to tune the interrogation signal frequency to the resonant frequency of the acoustical resonator incorporated into the thin film deposition sensor. The frequency data produced by frequency discriminator 176 may be coded as two binary values of RF/no RF and high/low. Alternatively, the frequency discriminator data may be digitized by an analog-to-digital converter, in which case the interrogator circuit may be informed of the actual output voltage of frequency discriminator 176. In some embodiments, the frequency discriminator output may be used to vary the duty cycle of a rectangular wave, where, for example, a 50% duty cycle may correspond to the sensor FBAR resonator frequency. An auxiliary "carrier detect" signal may be used to distinguish between the case where the interrogation frequency corresponds to the sensor FBAR resonant frequency and the case where the interrogation frequency is outside of the bandwidth of frequency discriminator 176.

In another embodiment, an FBAR resonator may be frequency modulated at an audio frequency and the resulting FM sidebands may be detected. Two FBAR resonators operating at different frequencies may be switched to produce a frequency shift keying (FSK) modulation on the return signal. In one embodiment, an integrated circuit may be configured to switch between the two FBAR resonators. An interrogator circuit may be configured to synchronously demodulate the return signal by locking onto a pilot tone modulated on the interrogation beam so that the interrogator circuit may use the same clock to recover the modulation.

In another embodiment, the FSK modulation may be incorporated into the interrogation source.

Still other embodiments are within the scope of the claims.

What is claimed is:

1. A system for monitoring a thin film deposition, comprising a thin film deposition sensor comprising a first thin film bulk acoustical resonator (FBAR) having an exposed surface and being responsive to thin film material deposits on the exposed surface and a second FBAR thermally coupled to the first acoustical resonator and shielded from deposition of thin film material, wherein the first FBAR and the second FBAR are formed on a common semiconductor substrate.

2. The system of claim 1, wherein the first and second acoustical resonators are coupled together by an electrical connection shielded from thin film material deposits.

3. The system of claim 1, further comprising an antenna configured to enable the thin film deposition sensor to be interrogated wirelessly.

4. The system of claim 1, wherein each of the first FBAR and the second FBAR has a thin film stack structure formed on a first surface of the semiconductor substrate and comprises a piezoelectric layer disposed between a pair of electrode layers, the first FBAR including an isolation cavity formed on a second surface of the semiconductor substrate opposite the first surface and a deposition shield disposed over the isolation cavity and having an exposed surface corresponding to the exposed surface of the first FBAR.

5. The system of claim 1, wherein each of the first FBAR and the second FBAR has a thin film stack structure formed on a first surface of the semiconductor substrate and comprises a piezoelectric layer disposed between a pair of electrode layers, the first FBAR including an isolation cavity extending through the semiconductor substrate to a second surface of the semiconductor substrate opposite the first surface, the thin film stack structure of second FBAR being disposed over an isolation cavity formed in the first surface of the semiconductor substrate.

6. A system for monitoring a thin film deposition, comprising a thin film deposition sensor comprising an acoustical resonator having an exposed surface and being responsive to thin film material deposits on the exposed surface, wherein the thin film deposition sensor further comprises a second acoustical resonator thermally coupled to the first acoustical resonator and shielded from deposition of thin film material, and the first and second acoustical resonators are coupled electrically in series.

7. The system 6, wherein the first and second acoustical resonators are thin film bulk acoustical resonators.

8. A system for monitoring a thin film deposition, comprising:
    a thin film deposition sensor having an exposed surface exposed and being responsive to thin film material deposits on the exposed surface, wherein the deposition sensor comprises a thin film bulk acoustical resonator (FBAR) formed on a semiconductor substrate and having an exposed surface corresponding to the exposed surface of the deposition sensor; and
    a transceiver circuit configured to enable the thin film deposition sensor to be interrogated wirelessly.

9. The system of claim 8, further comprising a first antenna coupled to the thin film deposition sensor and a second antenna coupled to the transceiver circuit.

10. The system of claim 9, wherein the second antenna is operable to transmit electromagnetic signals to the first antenna and to detect electromagnetic signals transmitted from the first antenna in response to excitation of the thin film deposition sensor by signals received from the second antenna.

11. The system of claim 8, wherein the transceiver circuit comprises an opto-electronic transducer.

12. The system of claim 8, wherein the thin film deposition sensor further comprises a second FBAR thermally coupled to the first FBAR and shielded from deposition of thin film material.

13. The system of claim 12, wherein the first FBAR and the second FBAR are coupled electrically in series.

14. The system of claim 12, wherein the first FBAR and the second FBAR are coupled together by an electrical connection shielded from thin film material deposits.

15. The system of claim 12, further comprising a plurality of pairs of exposed and shielded FBARS disposed on an elongated substrate.

16. The system of claim 15, wherein the FBARs of each pair are coupled electrically in series and the pairs of FBARs are inter-coupled electrically in parallel.

17. The system of claim 12, wherein each of the first FBAR and the second FBAR has a thin film stack structure formed on a first surface of the semiconductor substrate and comprises a piezoelectric layer disposed between a pair of electrode layers, the first FBAR including an isolation cavity formed on a second surface of the semiconductor substrate opposite the first surface and a deposition shield disposed over the isolation cavity and having an exposed surface corresponding to the exposed surface of the first FBAR.

18. The system of claim 12, wherein each of the first FBAR and the second FBAR has a thin film stack structure fanned on a first surface of the semiconductor substrate and comprises a piezoelectric layer disposed between a pair of electrode layers, the first FBAR including an isolation cavity extending through the semiconductor substrate to a second surface of the semiconductor substrate opposite the first surface, the thin film stack structure of second FBAR being disposed over an isolation cavity formed in the first surface of the semiconductor substrate.

19. The system of claim 12, wherein the optical transceiver circuit is mounted within a thin film deposition chamber.

20. The system of claim 8, wherein the transceiver circuit is an RFID tag circuit.

21. The system of claim 20, wherein the RFID circuit is electrically coupled to the thin film deposition sensor and comprises a power converter/transceiver, a modulator/demodulator circuit, a frequency discriminator, and a non-volatile memory.

22. A method of monitoring a thin film deposition on a substrate, comprising:
    disposing within a deposition chamber a thin film deposition sensor comprising a first thin film bulk acoustical resonator (FBAR) having an exposed surface and being responsive to thin film material deposits on the exposed surface and a second FBAR thermally coupled to the first acoustical resonator and shielded from deposition of thin film material, wherein the first FBAR and the second FBAR are formed on a common semiconductor substrate; and
    exposing a surface of the first acoustical resonator to a thin film deposition.

23. The method of claim 22, further comprising wirelessly interrogating the thin film deposition sensor to determine the resonant frequencies of the first FBAR and the second FRAR.

24. The method of claim 22, wherein wirelessly interrogating comprises transmitting an optical signal through an optical port of the deposition chamber.

25. The method of claim 22, wherein the thin film deposition sensor is disposed within the deposition chamber by attaching the thin film deposition sensor to a surface of the substrate, wherein the thin film deposition sensor is supported on the substrate surface.

26. A system for monitoring a thin film deposition, comprising a thin film deposition sensor comprising an acoustical resonator having an exposed surface and being responsive to thin film material deposits on the exposed surface, wherein the thin film deposition sensor further comprises a second acoustical resonator thermally coupled to the first acoustical resonator and shielded from deposition of thin film material, and further comprising a plurality of pairs of exposed and shielded acoustical resonators disposed on an elongated substrate, wherein the acoustical resonators of each pair are coupled electrically in series and the pairs of acoustical resonators are inter-coupled electrically in parallel.

27. A system for monitoring a thin film deposition, comprising a thin film deposition sensor comprising a thin film bulk acoustical resonator having an exposed surface and being responsive to thin film material deposits on the exposed surface, wherein the thin film deposition sensor further comprises a second thin film bulk acoustical resonator thermally coupled to the first thin film bulk acoustical resonator and shielded from deposition of thin film material, and further comprising a plurality of pairs of exposed and shielded thin film bulk acoustical resonators disposed on an elongated substrate.

* * * * *